United States Patent [19]

Meier

[11] Patent Number: 5,194,671
[45] Date of Patent: Mar. 16, 1993

[54] PROCESS FOR THE PREPARATION OF β-KETOCARBOXYLIC ACID ESTERS

[75] Inventor: Josef Meier, Burghausen, Fed. Rep. of Germany

[73] Assignee: Wacker-Chemie GmbH, Munich, Fed. Rep. of Germany

[21] Appl. No.: 849,534

[22] Filed: Mar. 11, 1992

[30] Foreign Application Priority Data

May 23, 1991 [DE] Fed. Rep. of Germany ....... 4116906

[51] Int. Cl.$^5$ .............................................. C07C 69/74
[52] U.S. Cl. ..................................... 560/126; 560/51; 560/174; 554/115
[58] Field of Search ......................... 560/174, 51, 126; 554/115

[56] References Cited

U.S. PATENT DOCUMENTS

| 2,661,374 | 12/1953 | Schechter | 560/174 |
| 2,948,747 | 8/1960 | Karbum | 560/174 |
| 3,142,692 | 7/1964 | Maggiulli | 560/174 |
| 3,565,928 | 2/1971 | Hagarty | 560/174 |

OTHER PUBLICATIONS

Harper, J. Chem. Soc., pp. 892–895 (1946).

*Primary Examiner*—Michael L. Shippen
*Attorney, Agent, or Firm*—Burgess, Ryan & Wayne

[57] ABSTRACT

The invention relates to a process for the preparation of β-ketocarboxylic acid esters of the general formula

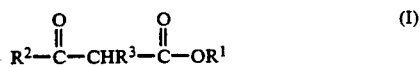

in which $R^1$ is an alkyl radical having 1 to 4 C atoms, $R^2$ is an alkyl radical or alkenyl radical having 2 to 15 C atoms or a phenyl radical and $R^3$ is hydrogen or an alkyl or alkenyl radical having 1 to 6 C atoms, characterized in that acetocarboxylic acid esters of the general formula

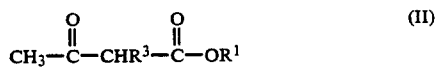

in which $R^1$ and $R^3$ are as defined, are reacted with calcium hydroxide or calcium oxide in the presence of an organic solvent and in the absence of water, the calcium chelate complexes formed are acylated with carboxylic acid chloride and the products are then cleaved with aqueous ammonium salt solution to form the β-ketocarboxylic acid esters of formula (I).

The β-ketocarboxylic acid esters readily accessible by the process according to the invention can be used as important intermediates in the synthesis of pharmaceutically active ingredients or plant protection agents.

15 Claims, No Drawings

PROCESS FOR THE PREPARATION OF β-KETOCARBOXYLIC ACID ESTERS

BACKGROUND OF THE INVENTION

1. Field of the Invention

The invention relates to a process for the preparation of β-ketocarboxylic acid esters starting from acetocarboxylic acid esters and carboxylic acid chlorides.

2. Description of the Related Art

A number of processes are known for the preparation of β-ketoesters. Thus, for example, carboxylic acid esters as the carbonyl component are reacted with CH-acidic carboxylic acid esters to give β-ketocarboxylic acid esters using at least equimolar amounts of bases such as, for example, sodium hydride, sodium amide and alkali metal alcoholates, in an inert solvent. Mixed ester condensation reactions are generally carried out only with formic acid esters as the carbonyl component because otherwise mixed reaction products are formed. However, the yields achieved here are relatively low because the β-ketoester formed in the condensation reaction has a higher reactivity than the starting compounds to be converted, which can lead to numerous secondary reactions. Such preparative processes are described in U.S. Pat. Nos. 2,407,942 and 2,367,632.

Furthermore, German patent document A-2412784 describes the condensation of CH-acidic dialkyl ketones with dialkyl carbonates, using at least equimolar amounts of base, in order to prepare β-ketoesters. However, the process has the disadvantage that highly toxic hexamethylphosphorotriamide (HMPT) has to be used as a solvent in order to achieve good yields.

J. Am. Chem. Soc. 67, 2198 (1945) describes the acylation of sodium acetoacetic acid esters with carboxylic acid chlorides and the cleavage of the resulting acylacetoacetic acid ester with ammonia or sodium methylate to give the β-ketoester. The yields achieved, however, are only of the order of 30 to 40%.

It is known from British patent document B-1000709 and Helv. 35, 2280(1952) to prepare β-ketoesters by reacting acetoacetic acid esters with carboxylic acid chlorides in the presence of magnesium alcoholates and then cleaving the 2-acylacetoacetic acid ester by hydrolysis. In practice, however, this method also has its difficulties. Thus, for example, the activity of commercially available magnesium alcoholate is inadequate, so that magnesium alcoholate needed for the reaction always has to be freshly prepared, but this requires the use of carbon tetrachloride, which is toxicologically very harmful.

The object was therefore to provide a process for the preparation of β-ketoesters which produces the β-ketoesters in good yields, in a simple and cost-effective manner, starting from readily accessible materials.

SUMMARY OF THE INVENTION

It has been found that β-ketoesters are obtained in very good yields by reacting acetocarboxylic acid esters with calcium hydroxide or calcium oxide in an inert solvent, acylating the calcium complex formed with carboxylic acid chloride and then cleaving the product with an ammonium salt solution to form β-ketoesters.

DESCRIPTION OF THE INVENTION

The invention relates to a process for the preparation of β-ketocarboxylic acid esters of the general formula

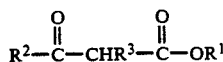

in which $R^1$ is an alkyl radical having 1 to 4 C atoms, $R^2$ is an alkyl radical or alkenyl radical having 2 to 15 C atoms or a phenyl radical and $R^3$ is hydrogen or an alkyl or alkenyl radical having 1 to 6 C atoms, characterized in that acetocarboxylic acid esters of the general formula

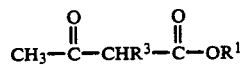

in which $R^1$ and $R^3$ are as defined, are reacted with calcium hydroxide or calcium oxide in the presence of an organic solvent and in the absence of water, the calcium chelate complexes formed are acylated with carboxylic acid chloride and the products are then cleaved with aqueous ammonium salt solution to form the β-ketocarboxylic acid esters of formula (I).

Preferred examples of the $R^1$ radicals are the methyl or ethyl radical. Suitable $R^2$ radicals are linear, branched or cyclic substituted or unsubstituted alkyl radicals or alkenyl radicals such as the ethyl, n-propyl, isopropyl, n-butyl, isobutyl, n-pentyl, isopentyl, hexyl, heptyl, cyclohexylmethyl, undecenyl or pentadecenyl radical. Further suitable $R^2$ radicals are substituted or unsubstituted phenyl radicals. Examples of $R^3$ are hydrogen or the methyl, ethyl or n-propyl radical. $R^3$ is preferably hydrogen.

To prepare the calcium chelate complex, the acetocarboxylic acid esters of formula (II) are reacted with calcium hydroxide or calcium oxide, preferably with calcium hydroxide. The calcium compounds are suspended in an organic solvent under anhydrous conditions, a good distribution of the reactants being ensured by mechanical movement. It is preferred to use aprotic solvents, examples being chlorinated hydrocarbons such as methylene chloride, 1,1,1-trichloroethane and trichloroethylene. It is also possible to use aromatic hydrocarbons such as benzene or toluene, ethers such as diethyl ether, diisopropyl ether or tetrahydrofuran, or ketones such as isopropyl methyl ketone or isobutyl methyl ketone. Methylene chloride or mixtures of said solvents with methylene chloride are particularly preferred.

The reaction takes place at temperatures of 0° to about 50° C., preferably at about 20° to about 30° C., the reaction mixture being kept at the reaction temperature by cooling. The calcium compound is preferably used in at least an equivalent amount based on the acetocarboxylic acid ester, particularly preferably in excess and especially in an excess of up to 5 mol %.

To introduce the radical $R^2$, the calcium chelate complex prepared in the preliminary step is acylated with the appropriate carboxylic acid chloride. The carboxylic acid chloride is preferably added to the suspension in at least an equivalent amount, particularly preferably in excess and especially in an excess of about 10 to about 20 mol %, based in each case on the acetocarboxylic acid ester. The reaction temperature is about 0° to about 50°, preferably about 30° to about 40° C.

To form the desired β-ketocarboxylic acid esters of general formula (I), the suspension is then treated with an aqueous solution of an ammonium salt, preferably ammonium formate, ammonium acetate or ammonium chloride, and particularly preferably with an aqueous ammonium chloride solution. The ammonium salt concentration in the solution is preferably about 10 to about 20% by weight. The ammonium salt is preferably used in an approximately equimolar amount based on the acetocarboxylic acid ester. The pH in the suspension is adjusted to 8.8 to 9.5 by the addition of a base, preferably ammonia or water-soluble primary or secondary amines, and particularly preferably aqueous ammonia. The reaction proceeds to form the β-ketocarboxylic acid ester at temperatures in the range of from 0° to about 50° C., preferably about 30° to about 40° C. When the reaction has ended, the β-ketocarboxylic acid ester formed can be isolated by conventional techniques such as extraction or evaporation, and then purified further, for example by fractional distillation.

The β-ketocarboxylic acid esters readily accessible by the process according to the invention can be used as important intermediates in the synthesis of pharmaceutically active ingredients or plant protection agents. In particular, ethyl propionylacetate is also suitable as a raw material for biologically degradable polymers.

The process according to the invention is illustrated in greater detail in the following Examples:

EXAMPLE 1

77.8 g (1.05 mol) of calcium hydroxide were placed in 550 ml of methylene chloride, and 116 g (1.0 mol) of methyl acetoacetate were added dropwise at 20° to 30° C. over 20 minutes, with vigorous stirring. Stirring was then continued for half an hour. 122.6 g (1.15 mol) of butyryl chloride were then metered into the thick suspension at a temperature of 30° to 35° C. over 1.5 hours. Stirring was then continued for 2 hours at 40° C. 56.2 g (1.05 mol) of ammonium chloride in 350 ml of water were then added to the reaction mixture at 30° C. and the resulting mixture was stirred for half an hour. After the pH had been adjusted to 8.9–9.0 by the addition of aqueous ammonia, the mixture was stirred for a further 3 hours at 30° to 35° C. The reaction mixture was then acidified with concentrated hydrochloric acid (pH 0.5–1.0) and washed with sodium bicarbonate solution and water. After separation of the aqueous phase, the methylene chloride was distilled off on an evaporator. This gave 134 g (GC purity 84%) of methyl butyrylacetate as a yellowish liquid (yield 78%).

EXAMPLE 2

56 g (1 mol) of calcium oxide were placed in 650 ml of methylene chloride, and 116 g (1 mol) of methyl acetoacetate were added dropwise at 20° to 30° C. over 0.5 hour. Stirring was then continued for 1 hour at this temperature. 116 g (1.05 mol) of butyryl chloride were then metered in at a temperature of 30°–35° C. over one hour and stirring was then continued for 3 hours at this temperature. 54 g (1 mol) of ammonium chloride in 300 ml of water were then added to the viscous suspension at 30° C. and the resulting mixture was stirred for 30 minutes. The pH of the reaction mixture was adjusted to 9 with aqueous ammonia and stirring was continued for 3 hours at 30° C. After the reaction mixture had been acidified with concentrated hydrochloric acid (pH<1), it was washed with sodium bicarbonate solution and water. After separation of the water phase, the solvent was distilled off on an evaporator. This gave 141 g (GC purity 73%) of methyl butyrylacetate (yield 71%).

EXAMPLE 3

Under the same conditions as in Example 1, 116 g (1.0 mol) of methyl acetoacetate in a mixture of 520 ml of methylene chloride and 30 ml of methyl ethyl ketone were reacted with 77.8 g (1.05 mol) of calcium hydroxide and 106.5 g (1.15 mol) of propionyl chloride. The pH in the subsequent reaction with ammonia was adjusted to 9.1. This gave 117 g (GC purity 79.0%) of methyl propionylacetate (yield 71.0%).

EXAMPLE 4

Under the same conditions as in Example 1, 116 g (1.0 mol) of methyl acetoacetate in a mixture of 520 ml of methylene chloride and 30 ml of methyl ethyl ketone were reacted with 77.8 g (1.05 mol) of calcium hydroxide and 122.6 g (1.15 mol) of isobutyryl chloride. The pH in the subsequent reaction with ammonia was adjusted to 9.2. This gave 136 g (GC purity 79.8%) of methyl isobutyrylacetate (yield 75.4%).

EXAMPLE 5

Under the same conditions as in Example 1, 116 g (1.0 mol) of methyl acetoacetate in a mixture of 520 ml of methylene chloride and 30 ml of methyl ethyl ketone were reacted with 77.8 g (1.05 mol) of calcium hydroxide and 138.7 g (1.15 mol) of valeryl chloride. The pH in this gave 151 g (GC purity 82.5%) of methyl valerylacetate (yield 79.0%).

EXAMPLE 6

Under the same conditions as in Example 1, 116 g (1.0 mol) of methyl acetoacetate in a mixture of 520 ml of methylene chloride and 30 ml of methyl ethyl ketone were reacted with 77.8 g (1.05 mol) of calcium hydroxide and 148.0 g (1.1 mol) of hexanoyl chloride. The pH in the subsequent reaction with ammonia was adjusted to 9.2. This gave 165 g (GC purity 78.5%) of methyl hexanoylacetate (yield 75.0%).

EXAMPLE 7

Under the same conditions as in Example 1, 116 g (1.0 mol) of methyl acetoacetate in a mixture of 520 ml of methylene chloride and 30 ml of methyl ethyl ketone were reacted with 77.8 g (1.05 mol) of calcium hydroxide and 176.7 g (1.1 mol) of cyclohexylacetyl chloride. The subsequent reaction time after the ammonia had been metered in was 6 hours at a pH of 9.5. This gave 196 g (GC purity 75.0%) of methyl 4-cyclohexylacetoacetate (yield 74.5%).

EXAMPLE 8

Under the same conditions as in Example 1, 130 g (1.0 mol) of ethyl acetoacetate in a mixture of 1.2 l of methylene chloride and 300 ml of methyl ethyl ketone were reacted with 77.8 g (1.05 mol) of calcium hydroxide and 106.5 g (1.15 mol) of propionyl chloride. The subsequent reaction time after the ammonia had been metered in was 4 hours at a pH of 9.3. This gave 134 g (GC purity 72.0%) of ethyl propionylacetate (yield 67.0%).

After fractional distillation, the β-ketocarboxylic acid esters of the Examples could be obtained with a purity of 96 to 99%.

What is claimed is:

1. A process for the preparation of β-ketocarboxylic acid esters of the general formula

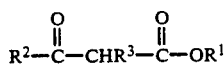

in which $R^1$ is an alkyl radical having 1 to 4 C atoms, $R^2$ is an alkyl radical or alkenyl radical having 2 to 15 C atoms or a phenyl radical and $R^3$ is hydrogen or an alkyl or alkenyl radical having 1 to 6 C atoms, which comprises reacting acetocarboxylic acid esters of the general formula

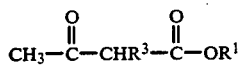

in which $R^1$ and $R^3$ are as defined, with calcium hydroxide or calcium oxide in the presence of an organic solvent and in the absence of water, the calcium chelate complexes formed are acylated with carboxylic acid chloride and the products are then cleaved with aqueous ammonium salt solution to form the β-ketocarboxylic acid esters of formula (I).

2. A process according to claim 1, wherein acetoacetic acid esters are used as the acetocarboxylic acid esters.

3. A process according to claim 1 wherein calcium hydroxide is used to prepare the calcium chelate complex.

4. A process according to claim 1, wherein the calcium compound is used in at least an equivalent amount based on the acetocarboxylic acid ester.

5. A process according to claim 1 wherein aprotic solvents are used.

6. A process according to claim 1 wherein methylene chloride or mixtures with methylene chloride are used as the solvents.

7. A process according to claim 1, wherein the carboxylic acid chloride is added to the suspension in at least an equivalent amount based on the acetocarboxylic acid ester.

8. A process according to claim 1 wherein the cleavage of the acylated calcium chelate complex takes place in aqueous ammonium chloride solution at a pH of 8.8 to 9.5.

9. A process according to claim 1 wherein the β-ketocarboxylic acid ester is methyl butylacetate.

10. A process according to claim 1 wherein the βketocarboxylic acid ester is methyl propionylacetate.

11. A process according to claim 1 wherein the β-ketocarboxylic acid ester is methyl isobutyrylacetate.

12. A process according to claim 1 wherein the β-ketocarboxylic acid ester is methyl valerylacetate.

13. A process according to claim 1 wherein the β-ketocarboxylic acid ester is methyl hexanoylacetate.

14. A process according to claim 1 wherein the β-ketocarboxylic acid ester is methyl cyclohexylacetoacetate.

15. A process according to claim 1 wherein the β-ketocarboxylic acid ester is ethyl propionylacetate.

* * * * *